US005693592A

United States Patent [19]

Illingworth

[11] Patent Number: 5,693,592
[45] Date of Patent: Dec. 2, 1997

[54] METHOD OF CONTROLLING DORMANCY BREAK AND BLOOMING IN PERENNIALS

[75] Inventor: John Illingworth, Warrandyte, Australia

[73] Assignee: SST Australia Pty. Ltd., Warrandyte, Australia

[21] Appl. No.: 651,398

[22] Filed: May 22, 1996

[30] Foreign Application Priority Data

May 23, 1995 [AU] Australia ................... PN3099

[51] Int. Cl.$^6$ .......... A01N 31/02; A01N 37/00; A01N 37/12; A01N 37/18
[52] U.S. Cl. .......... 504/118; 504/149; 504/313; 504/339; 504/351; 504/353
[58] Field of Search ............ 504/118, 142, 504/144, 149, 313, 318, 339, 353, 351

[56] References Cited

U.S. PATENT DOCUMENTS

| | | | |
|---|---|---|---|
| 3,940,419 | 2/1976 | Diehl et al. | 260/326 A |
| 3,984,570 | 10/1976 | Bent et al. | 424/341 |
| 4,017,299 | 4/1977 | Diehl et al. | 71/96 |
| 4,124,375 | 11/1978 | Bollinger et al. | 71/96 |
| 4,818,274 | 4/1989 | Bridle et al. | 71/106 |
| 5,228,899 | 7/1993 | Itoh et al. | 504/115 |
| 5,242,891 | 9/1993 | Larsen et al. | 504/127 |
| 5,346,879 | 9/1994 | Manabe et al. | 504/115 |

FOREIGN PATENT DOCUMENTS

| | | |
|---|---|---|
| 41688/78 | 5/1979 | Australia. |
| 22827/83 | 7/1984 | Australia. |
| 91/18508 | 12/1991 | WIPO. |
| 96/01049 | 1/1996 | WIPO. |

OTHER PUBLICATIONS

Saure, M.C., Dormancy Release in Deciduous Fruit Trees, *Horticultural Review*, 7, pp. 239–287, AVI Publ. Co., 1985.
Fernandez–Escobar & Martin, Chemical Treatments for Breaking Rest in Peach, etc., *J.Hort.Sci*, pp. 457–461 1987.

*Primary Examiner*—S. Mark Clardy
*Attorney, Agent, or Firm*—Emrich & Dithmar

[57] ABSTRACT

A method of controlling blooming in dormant perennial plants which method includes application to the dormant perennial plant of a composition including a growth regulating compound selected from the group consisting of fatty acid esters, fatty acid amides, fatty alcohols, fatty alcohol alkoxylates, phthalate esters, phthalic acid amides and imides and mixtures of two or more thereof.

17 Claims, No Drawings

METHOD OF CONTROLLING DORMANCY BREAK AND BLOOMING IN PERENNIALS

The present invention relates to a method for regulating the blooming of the flower buds and to a composition for use in regulating plant growth.

The regulation of plant growth can provide a significant improvement in the management of food crops allowing production at a lower cost or under conditions where the specific crops would not otherwise be commercially viable. In the commercial production of fruit for example, it is beneficial to have the fruit form at the same time on a tree as this allows the fruit to develop to maturity at about the same rate. The consumer generally demands large uniformly sized fruit and wide spread in fruit maturity is undesirable and costly as requires the farmer to conduct several harvests or waste a high proportion of the crop. Fruit bearing trees and vines require winter chilling to end the dormant state of the flower buds and to induce bud break and flower development. The amount of chilling required varies between fruit type and also the particular variety within a fruit type. If less than required chilling is achieved as a result of variation in the growing season or cultivation in mild or warm climatic regions several undesirable outcomes can result such as uneven or staggered blossoming, insufficient fruit set, poor leaf cover, reduced fruit size and uneven and extended time of fruit maturity. This is particularly a problem in growing areas such as Western Australia or Western America where frosts cannot be relied on to induce blooming.

Chemicals have been used to induce bud break. Compositions containing 4,6-dinitro-o-cresol(DNOC), which is a herbicide and insecticide, have been used to promote bud break and more uniform fruit development for many years. However, DNOC is a cumulative poison and skin contact can lead to local necrosis and dangerous systemic effects (The Merck Index, Ninth Edition 1980). These toxicology problems have lead to deregulation of DNOC for agricultural use in some countries. Another product based on hydrogen cyanamide has been trialed but is also unfavourable due to its toxicity and corrosive nature.

Many other chemicals have been found to effect dormancy break and the most promising are summarised in Saure, M.C., "Dormancy Release in Deciduous Fruit Trees" *Horticultural Review*, 7, pp. 239–287, AVI Publishing Co. Inc. Westport, Conn. (1985). Examples are Thiourea, Gibberellic Acid, cytokinins, and Nitrogen compounds such as potassium nitrate however the results are mixed. An article demonstrating the effect of potassium nitrate is Fernandez-Escobar, R. and Martin R., "Chemical Treatments for Breaking Rest in Peach in Relation to Accumulated Chilling," *J. Hort. Sci.*, 62(4), pp. 457–461, (1987).

There is a need for a plant growth regulating method and composition which is effective in inducing bud break in plants, particularly fruit trees, and is safe to use.

According to the present invention we provide a method of controlling blooming in dormant perennial plants, particularly fruit trees, which method includes application to at least a part of the plants of a composition including a growth regulating compound selected from the group consisting of fatty acid esters, fatty acid amides, fatty alcohols and fatty alcohol alkoxylates and mixtures of two or more thereof.

The most preferred growth regulating compounds are fatty acid esters, fatty acid amides and mixtures thereof.

We have found that a mixture of a fatty alcohol, fatty acid ester or amide with a phthalate ester, amide or imide exhibits a surprising level activity. We therefore provide in accordance with a further aspect of the invention a plant growth regulating composition including a fatty alcohol, fatty acid ester or fatty acid amide and a phthalate derivative selected from phthalate esters, phthalate amides and phthalate imides.

The preferred fatty alcohols are $C_6$–$C_{20}$ fatty alcohols. The preferred fatty acid esters are those wherein the acid portion of the ester is a $C_8$–$C_{32}$ fatty acid (more preferably $C_{12}$–$C_{32}$ fatty acid) and the alcohol portion is a $C_1$–$C_{12}$ hydrocarbyl alcohol or polyol. Examples of said hydrocarbyl alcohol or polyol include $C_1$–$C_{22}$ alkanol and alkylene glycols or condensation products having 1 to 20 moles of alkylene oxide (more preferably ethylene oxide, propylene oxide or butylene oxide or mixtures of two or more thereof). More preferred hydrocarbyl alcohol or polyol are $C_1$ to $C_{12}$ alkanol and alkylene glycols or condensation products having 2 to 6 moles of ethylene oxide. In the case of fatty acid amides, the fatty acid portion is preferably as defined above and the amine portion is preferably a mono or di substituted amino group wherein the amine substituents are one or two independently selected $C_1$–$C_{12}$ hydrocarbyl groups. Specific examples of fatty acids include lauric acid, tridecic acid, myristic acid, palmitic acid, stearic acid, oleic acid, linoleic acid, linolenic acid and eicosanoic acid. Alkyl esters of the fatty acid are preferred particularly $C_1$–$C_8$ alkyl and more preferably $C_1$ to $C_4$ alkyl esters such as the methyl, ethyl, propyl, isopropyl, butyl and isobutyl esters. The most preferred fatty acid esters are the $C_1$–$C_4$ alkyl esters of oleic acid, particularly methyl oleate and ethyl oleate.

Preferred phthalic acid esters are esters wherein the acid portion is a substituted or unsubstituted phthalic acid or anhydride and is mono- or di- esterified with a $C_1$–$C_{12}$ hydrocarbyl alcohol or polyol. Preferred phthalic acid amides are compounds wherein the amine derived portion of the amide is amino substituted with one or two groups selected from $C_1$–$C_{12}$ hydrocarbyl and hydroxy substituted $C_1$–$C_{12}$ hydrocarbyl. In the case of phthalate imides the imino nitrogen is preferably substituted with $C_1$–$C_{12}$ hydrocarbyl or hydroxy substituted $C_1$–$C_{12}$ hydrocarbyl. Preferred hydrocarbyl groups are $C_1$–$C_{12}$ alkyl and preferred hydroxy substituted alkyl groups are hydroxy $C_1$–$C_{12}$ alkyl. The most preferred phthalate esters are di-($C_1$–$C_{12}$ alkyl) phthalate such as dibutyl phthalate (phthalic acid dibutyl ester) and dioctyl phthalates particularly di-(2-ethylhexyl)phthalate.

The most preferred compositions of the invention therefore include at least one $C_1$–$C_{12}$ alkyl ester of a $C_{12}$–$C_{32}$ fatty acid and a di-($C_1$–$C_{12}$ alkyl ester) of phthalic acid.

The preferred compositions of the invention include one or more surfactants which have been found to aid in preparation of the composition and may assist in penetration of the active components. Many types of surfactant can aid in the preparation of the composition including anionic, cationic and amphoteric surfactants however the preferred surfactants are non-ionic surfactants such as:

Polyoxypropylene polyoxyethylene block copolymers,
Alkyl aryl ethoxylates and or alkoxylates,
Fatty acid ethoxylates and or alkoxylates,
Fatty alcohol ethoxylates and or alkoxylates,
Fatty amine ethoxylates and or alkoxylates,
Vegetable or seed oil ethoxylates and or alkoxylates,
Sorbitan fatty acid ester ethoxylates and or alkoxylates, and
Alkyl polysaccharides.

Specific examples of suitable non-ionic surfactants include a block copolymer of polyoxypropylene (PO) and polyoxyethylene (EO) in the molar ratio of about 28:6.

Another useful surfactant is a nonyl phenyl ether of polyoxyethylene (EO) which contains, on average, about 5 moles of polyoxyethylene per mole of nonylphenyl.

When a mixture of fatty acid ester and phthalate ester is used in the compositions of the present invention preferably the weight ratio of these components is from 5:95 to 100:0 (preferably to 95:5) with the preferred ratio being from 80:20 to 20:80.

Typically the total surfactant concentration in the composition of the invention will be in the range of from 0–40% by weight but preferably will be present in at least 0.1%.

The composition of the invention may be formulated in a wide range of forms known in the art. The composition may, for example, be in the form of a concentrate to be diluted prior to application and may be in the form of a granule powder or liquid with a suitable solid or liquid carrier. For example, the formulation may be in the form of an emulsion or dispersion in water and may comprise solvents or agricultural chemicals. Alternatively formulation may be adapted to form an emulsion when diluted with water prior to use. The composition may typically contain from 0.5 to 95% by weight of the plant growth regulating compound. In one embodiment the composition contains water as a diluent so that the active components comprises in the range of from 0.5–50% by weight of the diluted formulation. Higher concentrations of growth regulating compound may be present in the composition when, for example, it is in a form suitable for use as an ultra low volume spray which may merely contain the active agents and generally also a surfactant component. Preferably the composition of the invention is applied at a rate of from 20 to 160 liters per hectare based on the dry volume of the composition The compositions of the invention have been found to be effective in promoting bud break when applied during the dormant period of fruit trees. The compositions have also been found to be effective in retarding or setting back bud break and flowering if applied late in the dormant period or during early green tip. The compositions have also been found to cause compaction of the flowering period, particularly if applied at about 35–45 days before bud break. To achieve bud break it is preferred that the composition be added with an aqueous diluent at a rate in the range of from 10–5000 liters per hectare based on the volume of the dilute composition containing the growth regulating compound, such as fatty acid ester, and surfactant components.

The process of the present invention is useful for bring forward or setting back the time of bud break on fruit trees and various other plants. It is likely that the optimum time of application to achieve the desired outcomes will vary dependant upon local environmental and regional conditions.

To bring forward dormancy break and bud burst it is preferred that trees be sprayed from 10 to 60 days before expected bud break. The more preferred time of application is 20 to 50 days and most preferably 35–45 days before bud break.

To set back bud break and/or flowering it is preferred that the tree be sprayed from full bloom to 28 days more preferably 20 days before expected bud break. The preferred time of application being 0 to 15 days before bud break.

Examples of the types of plants to which the present invention is applicable are:

All perennial fruit crops such as (but not limited to):
Pome fruits, eg. apples, pears
Stone fruits eg. plums, cherries, nectarines, peaches
Vines, grapes, olives
Temperate fruits eg. Actinidia (Kiwi fruit, figs, morus)
Berries eg. strawberries, raspberries, cranberries, blackberries, loganberries
Nuts eg. almonds, walnuts, chestnuts It is preferred that the compositions of the invention are applied to the buds of the plant in which blooming is to be controlled and the method has been found to provide significant compaction of blooming, that is, the blooming of buds is more uniform.

The invention will now be further described by, but is in no way limited to, the following examples.

EXAMPLE 1

A composition of the invention was prepared by mixing the following components:

| Component | Proportion % w/w |
| --- | --- |
| Methyl Oleate | 40 |
| DiButyl Phthalate | 35 |
| (PO)28(EO)5.7 Block Copolymer | 10 |
| Nonyl Phenol + 5EO | 15 |

The above formulation was evaluated in trials in an apple orchard using application rates of 40 and 80 liters/2000L water/Ha.

COMPARATIVE EXAMPLE

The composition of the invention was compared with a composition comprising DNOC at a concentration of 40 liters of DNOC per 2000 liters of water per hectare and the results were also compared with a control which was unsprayed. Full details of the trial are provided below. The varieties of tree tested were Royal Gala, Gala and Fuji apples. The average age of the trees was eight years. Three replicates of the trials were conducted using single tree plots with a single tree buffer between them. The plots were randomly placed in the orchard.

Trial 1:

| Treatment Number | Treatment |
| --- | --- |
| 1 | Example 1 - 80 L/ha (4 L/100 L) |
| 2 | DNOC - 40 L/ha (2 L/100 L) + winter oil 2 L/100 L |
| 3 | CONTROL - (Unsprayed) |
| | Applied to the first tier with hand lance. |
| | Rate = 2000 L/ha |

Trial measurement:

Four measurements were carried out one week apart commencing at the onset of flowering. Four stages of growth were measured, Tight Cluster, Pink Bud, Full Bloom and Late Petal Fall and damage was assessed.

Analysis of Variance:

The percentage of flowers in full bloom in the first two periods (transformed data).

| Treatment | Royal Gala | Fuji | Gala |
| --- | --- | --- | --- |
| 1 | 71.3 | 65.1 | 54.5 |
| 2 | 69.6 | 70.0 | 59.5 |
| 3 | 17.8 | 29.4 | 37.0 |

Statistical analysis of the results showed that the percentage bloom figures for treatments 1 and 2 were not significantly different.

The results showed that at 80L/HA the composition of the invention performed at least as well as DNOC in inducing bloom. The composition of the invention however has a low toxicity when compared with DNOC and is safe for use in commercial operations.

Trial 2:

Several fruit varieties were treated at different times in four separate fruit growing districts in Western Australia in the month of August. Treatments were carried out on large sections of the orchards and five trees (replicates) were randomly selected within each section for assessment purposes.

In all cases the composition of Example 1 was applied at the rate of 80L/Ha in 2000L/Ha of water (ie. at 4L/100L) and was compared to an untreated control. Treatments were applied through a conventional horticultural spray mister.

Blossom counts were carried out at weekly intervals and the following parameters were measured and calculated:

(1) the number of days from the first count until 50% of buds have reached full bloom (time of bud burst).

This measures the extent to which bud burst was brought forward.

(2) the number of days from when 10% of the buds have bloomed until 90% of the buds have bloomed (uniformity of bud burst).

This measures the compacting effect of the treatment.

| | | | APPLES | | | | | | | |
|---|---|---|---|---|---|---|---|---|---|---|
| | | | Days to 50% Full Bloom | | | | Days from 10% to 90% FB | | | |
| Area | Property | Variety | Eg 1 | Control | Sig | ΔD | Eg 1 | Control | Sig | ΔD |
| 1 | A | Fuji | 4.07 | 6.76 | * | 2.69 | 8.95 | 12.84 | * | 3.89 |
| | | Pink Lady pruned | 3.63 | 10.58 | *** | 6.95 | 9.24 | 16.01 | ** | 6.77 |
| | | Pink Lady | 2.82 | 10.58 | *** | 7.76 | 6.49 | 16.01 | *** | 9.52 |
| 1 | B | Granny Smith | 8.36 | 9.86 | n/s | 1.50 | 10.13 | 15.78 | ** | 5.65 |
| 1 | C | Royal Gala | 9.35 | 10.84 | 0.06 | 1.49 | 12.98 | 11.90 | n/s | −1.08 |
| | | Golden Delicious | 11.49 | 15.23 | ** | 3.74 | 10.34 | 10.12 | n/s | −0.22 |
| 2 | D | Pink Lady | 8.64 | 17.17 | *** | 8.53 | 14.21 | 9.62 | 0.07 | −4.59 |
| | | Golden Delicious | 8.36 | 12.07 | *** | 3.71 | 11.18 | 11.15 | n/s | −0.03 |
| | | Royal Gala | 6.47 | 10.63 | *** | 4.16 | 11.15 | 11.08 | n/s | −0.07 |
| | | Fuji | 5.57 | 10.17 | *** | 4.60 | 10.85 | 8.93 | n/s | −1.92 |
| 2 | E | Granny Smith | 12.28 | 17.80 | *** | 5.52 | 11.08 | 11.81 | n/s | 0.73 |
| | | Red Delicious | 9.99 | 15.97 | *** | 5.98 | 10.13 | 20.55 | ** | 10.42 |
| 3 | F | Granny Smith | 3.46 | 2.96 | n/s | −0.50 | 7.95 | 11.45 | 0.08 | 3.50 |
| | | Golden Delicious | 4.36 | 6.70 | 0.08 | 2.34 | 9.51 | 9.65 | n/s | 0.14 |
| 3 | G | Fuji | 4.67 | 10.77 | *** | 6.10 | 10.03 | 8.36 | n/s | −1.67 |
| 3 | H | Pink Lady | 8.15 | 3.26 | ** | −4.89 | 10.71 | 10.82 | n/s | 0.11 |
| | | Red Delicious | 0.86 | 6.56 | *** | 5.70 | 6.97 | 10.92 | n/s | 3.95 |
| | | Royal Gala | 0.00 | 1.67 | * | 1.67 | 3.21 | 6.96 | ** | 3.75 |

Eg 1 refers to the composition of Example 1.

| | | | PEARS | | | | | | | |
|---|---|---|---|---|---|---|---|---|---|---|
| | | | Days to 50% Full Bloom | | | | Days from 10% to 90% FB | | | |
| Area | Property | Variety | Eg 1 | Control | Sig | ΔD | Eg 1 | Control | Sig | ΔD |
| 3 | H | Packham | 6.80 | 2.39 | *** | −4.41 | 11.46 | 6.99 | ** | −4.47 |
| 4 | I | Nashi | 4.53 | 7.90 | * | 3.37 | 10.35 | 9.70 | n/s | −0.65 |

| | | | CHERRIES | | | | | | | |
|---|---|---|---|---|---|---|---|---|---|---|
| | | | Days to 50% Full Bloom | | | | Days from 10% to 90% FB | | | |
| Area | Property | Variety | Eg 1 | Control | Sig | ΔD | Eg 1 | Control | Sig | ΔD |
| 3 | H | Bing | 0.00 | 5.94 | *** | 5.94 | 5.35 | 12.22 | *** | 6.89 |

The figures in the table above represent the means for sprayed and control treatments for parameters (1) and (2).

Sig indicates whether the means are significantly different.

\*\*\* significantly different, p<0.001

\*\* significantly different, p<0.01

\* significantly different, p<0.05

Number significance very close to p=0.05 n/s not significantly different

ΔD indicates the difference in mean days between sprayed and control treatments for parameters (1) and (2).

Note 1: Treatments applied in area 3 were carried out 2½ weeks later than ideal due to unfavourable climatic conditions. This in some cases had the effect of setting back the time to full bloom, particularly on Pink Lady apples and Packham pears.

Note 2: In area 3 property H Royal Gala apples and Bing cherries took zero days to 50% Full Bloom. This means that 50% of buds had reached Full Bloom on the first measurement date.

Trial 3 - Timing Trial

This trial demonstrates the effect of the timing of treatment on the control of blooming using the composition of Example 1.

|      |           |         | Days to 50% Full Bloom |         |     |     | Days from 10% to 90% FB |         |     |     |
|------|-----------|---------|------|---------|-----|-----|------|---------|-----|-----|
| Area | Treatment | Variety | Eg 1 | Control | Sig | ΔD  | Eg 1 | Control | Sig | ΔD  |
| 3    | 10 Aug    | Naga Fu No. 2 | 8.45 | >18 | * | >10 | 14.93 | >18 | *** | >3 |
|      | 22 Aug    | Naga Fu No. 2 | 10.08 | >18 | * | >8 | 7.70 | >18 | *** | >10 |
|      | 2 Sept    | Naga Fu No. 2 | 13.94 | >18 | * | >4 | 7.91 | >18 | *** | >10 |
|      | 5% LSD    |         | 4.33 |         | 5% LSD |  | 2.66 |   |    |    |

The control trees had achieved only 14% Full Bloom at the time of the final (fifth) cluster count (23 October) which was 18 days after the first cluster count (5 October). Figures based on measurement of six replicates.

|      |           |         | Days to 50% Full Bloom |         |     |     | Days from 10% to 90% FB |         |     |     |
|------|-----------|---------|------|---------|-----|-----|------|---------|-----|-----|
| Area | Treatment | Variety | Eg 1 | Control | Sig | ΔD  | Eg 1 | Control | Sig | ΔD  |
| 3    | 10 Aug    | Red Braeburn | 1.16 | 10.43 | *** | 9.27 | 6.95 | 10.61 | ** | 3.66 |
|      | 22 Aug    | Red Braeburn | 6.22 | 10.43 | *** | 4.21 | 8.80 | 10.61 | ** | 1.81 |
|      | 2 Sept    | Red Braeburn | 9.38 | 10.43 | *** | 1.05 | 5.20 | 10.61 | ** | 5.41 |
|      | 5% LSD    |         | 2.02 |         | 5% LSD |  | 3.26 |   |    |    |

Figures based on measurement of six replicates.

In this trial there was a significant linear relationship between day of treatment and days to reach 50% bud burst for both varieties. It was possible to estimate that for every 10 days delay in spraying bud burst was delayed 2.37 days for Naga Fu and 3.58 days for Red Braeburn.

Trial 4:

This trial relates to methods of the invention using compositions of Examples 1 to 7 prepared from the components in the percentages by weight shown.

|                              | Example |    |    |    |    |    |    |
|------------------------------|----|----|----|----|----|----|----|
| Component                    | 1  | 2  | 3  | 4  | 5  | 6  | 7  |
| Methyl Oleate                | 40 | 48 | 90 | 90 | —  | —  | —  |
| Dibutyl Phthalate            | 35 | 42 | —  | —  | 85 | 85 | —  |
| (PO)28(EO)5.7 Block Copolymer| 10 | —  | —  | —  | —  | —  | 50 |
| Nonyl phenol + 5EO           | 15 | —  | 10 | 10 | —  | —  | 5  |
| Castor Oil + 40EO            | —  | 4  | —  | —  | 12 | 12 | —  |
| Calcium Dodecyl Benzene Sulfonate | — | 6  | —  | —  | 3  | 3  | —  |
| Nonyl Alcohol + 2EO          | —  | —  | —  | —  | —  | —  | 25 |
| Nonyl Alcohol + 5EO          | —  | —  | —  | —  | —  | —  | 20 |

|      |           |         |        | Days to 50% Full Bloom |        | Days from 10% to 90% |        |
|------|-----------|---------|--------|--------|--------|--------|--------|
|      |           |         | Rate   |        |        |        |        |
| Area | Treatment | Variety | L/100 L | Result | ΔD    | Result | ΔD    |
| 3    | Example 1 | Gala    | 4      | 1.56   | 1.68   | 5.85   | 5.25   |
|      | Example 2 | Gala    | 35     | 2.39   | 0.85   | 7.17   | 3.93   |
|      | Example 3 | Gala    | 3.5    | 0.88   | 2.36   | 5.34   | 5.76   |
|      | Example 4 | Gala    | 1.75   | 4.32   | −1.08  | 10.40  | 0.70   |

-continued

|      |           |         |        | Days to 50% Full Bloom |        | Days from 10% to 90% |        |
|------|-----------|---------|--------|--------|--------|--------|--------|
|      |           |         | Rate   |        |        |        |        |
| Area | Treatment | Variety | L/100 L | Result | ΔD    | Result | ΔD    |
|      | Example 5 | Gala    | 3.5    | 6.36   | −3.12  | 10.26  | 0.84   |
|      | Example 6 | Gala    | 1.75   | 5.57   | −2.33  | 11.00  | 0.10   |
|      | Example 7 | Gala    | 1.75   | 1.56   | 1.68   | 7.04   | 4.06   |
|      | DNOC +    | Gala    | 0.5 + 0.5 | 5.95 | −2.71 | 10.12 | 0.98   |

-continued

| | | | Days to 50% Full Bloom | | Days from 10% to 90% | |
|---|---|---|---|---|---|---|
| Area | Treatment | Variety | L/100 L | Result | ΔD | Result | ΔD |
| | Winter Oil | | | | | | |
| | DNOC + Winter Oil | Gala | 2 + 2 | 6.57 | −3.33 | 6.84 | 4.26 |
| | Control | Gala | — | 3.24 | — | 11.10 | — |
| | Sig | | | <0.001 | | <0.001 | |
| | 5% LSD | | | 2.08 | | 2.50 | |

Figures based on measurement of three replicates.

| | | | Days to 50% Full Bloom | | Days from 10% to 90% | |
|---|---|---|---|---|---|---|
| Area | Treatment | Variety | L/100 L | Result | ΔD | Result | ΔD |
| 3 | Example 1 | Fuji | 4 | 5.06 | 1.62 | 8.48 | 0.89 |
| | Example 2 | Fuji | 3.5 | 2.38 | 4.30 | 8.49 | 0.88 |
| | Example 3 | Fuji | 3.5 | 3.44 | 3.24 | 8.98 | 0.39 |
| | Example 4 | Fuji | 1.75 | 7.06 | −0.38 | 11.75 | −2.38 |
| | Example 5 | Fuji | 3.5 | 7.00 | −0.34 | 10.64 | −1.27 |
| | Example 6 | Fuji | 1.75 | 8.47 | −1.79 | 9.84 | −0.47 |
| | Example 7 | Fuji | 1.75 | 4.31 | 2.37 | 9.75 | −0.38 |
| | DNOC + Winter Oil | Fuji | 0.5 + 0.5 | 8.27 | −1.59 | 9.97 | −0.60 |
| | DNOC + Winter Oil | Fuji | 2 + 2 | 7.35 | −0.67 | 7.15 | 2.22 |
| | Control | Fuji | — | 6.68 | — | 9.37 | — |
| | Sig | | | 0.036 | | 0.188 | |
| | 5% LSD | | | 3.78 | | 2.99 | |

Figures based on measurement of three replicates.
This set of trials demonstrate a number of key points.

1. Methyl oleate demonstrates good efficacy at 3.75L/100L and is clearly identified as the principal active ingredient in Example 1 to bring forward bud break.
2. Dibutyl Phthalate does not have a significant effect on bud break when applied alone.
3. The mixture of methyl oleate and dibutyl phthalate in Example 1 and 2 produce a synergistic performance that is not anticipated by assessing their individual behaviour as seen in Examples 4 and 6.
4. Ethoxylated nonyl alcohol demonstrates good efficacy as seen in Example 7.

This trial was carried out in area 3 which suffered from unfavourable weather conditions resulting in late application of the treatments. Earlier application is expected to produce a significant increase in the days brought forward for bud break and also tighter compaction results.

Trial 5:
On both varieties the trial design is a randomised complete block with four treatments - 2, 4 and 6L/100L of the composition of Example 1 and untreated control. There are six single tree replicates. The trees were treated on 2 September 1995 in the State of Victoria, Australia. Some buds were swelling and a few were green throughout the blocks. It should be noted that the spring was early by 7 to 10 days with regard to apple flowering times compared with average years. The weather was warm in late August and remained warmer than usual during spring.

Note: The results below are the means of the results in each treatment of six replicates as recorded 'n' days after treatment. Fishers test—means followed by different letters are significantly different P<0.05.

| | % Canopy Development - Granny Smith | | | | |
|---|---|---|---|---|---|
| Treatment | 24 DAT | 33 DAT | 43 DAT | 50 DAT | 71 DAT |
| 2 L/100 L | 6.3 A | 10.7 B | 24 A | 30 A | 53 AB |
| 4 L/100 L | 4.3 B | 6.8 C | 17 B | 26 AB | 58 A |
| 6 L/100 L | 3.3 B | 3.4 D | 9 C | 19 B | 47 B |
| Control | 6.6 A | 12.8 A | 28 A | 32 A | 49 AB |
| LSD P < 0.05 | 1.2 | 1.5 | 6 | 9 | 9 |

| | % Canopy Development - Imperial Gala | | | | |
|---|---|---|---|---|---|
| Treatment | 24 DAT | 33 DAT | 43 DAT | 50 DAT | 71 DAT |
| 2 L/100 L | 7.8 B | 12.2 B | 19 B | 24 AB | 45 A |
| 4 L/100 L | 5.8 C | 8.6 C | 14 C | 26 AB | 53 A |
| 6 L/100 L | 4.4 D | 4.7 D | 11 C | 23 B | 53 A |
| Control | 13.1 A | 15.5 A | 24 A | 28 A | 48 A |
| LSD P < 0.05 | 1.1 | 1.7 | 4 | 4 | 4 |

| | % Flower Buds Open to Bees - Granny Smith | | | |
|---|---|---|---|---|
| Treatment | 24 DAT | 33 DAT | 43 DAT | 50 DAT |
| 2 L/100 L | 37 AB | 31 A | 75 A | 91 A |
| 4 L/100 L | 22 BC | 19 A | 88 A | 92 A |
| 6 L/100 L | 9 C | 9 A | 75 A | 93 A |
| Control | 49 A | 31 A | 77 A | 93 A |
| LSD P < 0.05 | 26 | 24 | 18 | 8 |

| | % Flower Buds Open to Bees - Imperial Gala | | | |
|---|---|---|---|---|
| Treatment | 24 DAT | 33 DAT | 43 DAT | 50 DAT |
| 2 L/100 L | 31 B | 7.2 B | 68 AB | 88 B |
| 4 L/100 L | 13 C | 0.7 C | 63 BC | 95 A |
| 6 L/100 L | 0.5 D | 0.0 C | 50 C | 97 A |
| Control | 50 A | 28 A | 86 A | 96 A |
| LSD P < 0.05 | 7.1 | 4.7 | 18 | 5 |

*24 DAT result is for % flower buds at loose cluster/pink.
DAT means days after treatment It is clear from the results of this trial that the composition of Example 1 applied on Sep. 2, 1995 extended the dormant period of Granny Smith and Imperial Gala apple trees and resulted in a more concentrated flowering period. This even flowering has resulted in even fruit set compared with untreated trees. There was a gradation of response with the rate of 6L/100L having the most effect and 2L/100L having the least effect. The trees grew rapidly out of dormancy and caught up to untreated trees with regard to canopy development Finally, it is to be understood that various other modifications and/or alterations may be made without departing from the spirit of the present invention as outlined herein.

I claim:

1. A method of controlling dormancy break and blooming of dormant perennial plants which method comprises application to the dormant perennial plant of a composition comprising a growth regulating compound selected from the group consisting of fatty acid esters, fatty acid amides, fatty alcohols, fatty alcohol alkoxylates and mixtures of two or more thereof, wherein the composition is applied within 60 days before bud break would normally occur.

2. A method of according to claim 1 wherein the growth regulating compound is selected from the group consisting of:

$C_6$ to $C_{20}$ fatty alcohols;

fatty acid esters wherein the acid portion is a $C_8$ to $C_{32}$ fatty acid and the alcohol portion is a $C_1$ to $C_{12}$ hydrocarbyl alcohol or polyol; and fatty acid amides wherein the acid portion is a $C_8$ to $C_{32}$ fatty acid and the amine derived portion is a mono or di-($C_1$ to $C_{12}$ hydrocarbyl) amine.

3. A method according to claim 1 wherein the growth regulating compound comprises a fatty acid ester which is a $C_1$ to $C_8$ alkyl ester of a fatty acid selected from the group consisting of lauric acid, tridecic acid, myristic acid, palmitic acid, stearic acid, oleic acid, linoleic acid, linolenic acid and eicosanoic acid.

4. A method according to claim 3 wherein the growth regulating compound includes a fatty acid ester which is a $C_1$ to $C_4$ alkyl ester of oleic acid.

5. A method according to claim 1 wherein the plant growth regulating compound is a fatty acid ester selected from $C_1$ to $C_{12}$ alkyl esters of a $C_{12}$ to $C_{32}$ fatty acid and the composition further comprises a di-($C_1$ to $C_{12}$ alkyl) ester of phthalic acid.

6. A method according to claim 1 wherein the composition includes one or more surfactants.

7. A method according to claim 6 wherein the one or more surfactants are selected from the group consisting of alkylaryl ethoxylates and alkoxylates; fatty acid ethoxylates and alkoxylates; fatty alcohol ethoxylates and alkoxylates; fatty amine ethoxylates and alkoxylates; vegetable or seed oil ethoxylates and alkoxylates; sorbitan fatty ester ethoxylates and alkoxylates; and alkyl polysaccharides.

8. A method according to claim 7 wherein the surfactant is a block copolymer of poyoxypropylene and polyoxyethylene or is a nonyl phenol ether of polyoxyethylene.

9. A method according to claim 5 wherein said composition comprises in the range of from 0.5 to 95% by weight of a $C_1$ to $C_{12}$ alkyl ester of a $C_{12}$ to $C_{32}$ fatty acid or mixture of $C_1$ to $C_{12}$ alkyl ester of $C_{12}$ to $C_{32}$ fatty acid and a di-($C_1$ to $C_{12}$ alkyl ester) of phthalic acid.

10. A method according to claim 1 wherein the composition is applied at a rate of from 20 to 160 liters per hectare based on the dry volume of the composition.

11. A method according to claim 1 wherein the growth regulating compound is present at a concentration of from 0.5 to 95% by weight and surfactant is present in an amount of up to 40% by weight and the composition further includes water and is applied at a rate of from 10 to 5000 liters of composition per hectare based on the volume of the dilute composition.

12. A method according to claim 1 wherein the perennial plant is selected from pome fruit trees, stone fruit trees and vines.

13. A method according to claim 12 wherein the perennial plant is pear, apple, plum, cherry or grape vine.

14. A method according to claim 12 wherein blooming is brought forward by application of the composition.

15. A method according to claim 14 wherein the composition is applied from 20 to 50 days before bud break would normally occur.

16. A method according to claim 15 wherein the composition is applied from 35 to 45 days before bud break would normally occur.

17. A method according to claim 1 wherein the composition is applied in the period from 20 days before the time when bud break would normally occur up to the occurrence of green tip and bloom is thereby delayed.

* * * * *

UNITED STATES PATENT AND TRADEMARK OFFICE
CERTIFICATE OF CORRECTION

PATENT NO. : 5,693,592

DATED : December 2, 1997

INVENTOR(S) : John Illingworth

It is certified that error appears in the above-identified patent and that said Letters Patent is hereby corrected as shown below:

At column 6, in the table, change each reference to "Pink Lady" to –Pink Lady Brand Cripps Pink Cultivar–.

Signed and Sealed this

Sixth Day of July, 1999

Attest:

Q. TODD DICKINSON

*Attesting Officer*     *Acting Commissioner of Patents and Trademarks*